United States Patent [19]

Menard et al.

[11] Patent Number: 4,479,950

[45] Date of Patent: Oct. 30, 1984

[54] AROYLAMINOACID DISULFIDES

[75] Inventors: Paul R. Menard, Tuckahoe; Howard Jones, Ossining, both of N.Y.; John T. Suh, Greenwich, Conn.

[73] Assignee: USV Pharmaceutical Corporation, Tarrytown, N.Y.

[21] Appl. No.: 439,525

[22] Filed: Nov. 5, 1982

[51] Int. Cl.³ .............. A61K 31/195; A61K 31/215; C07C 149/40; C07C 149/41; C07D 401/12; C07D 407/12; C07D 409/12; C07D 413/12

[52] U.S. Cl. .................. 424/248.5; 424/258; 424/263; 424/267; 424/274; 424/275; 424/285; 424/309; 424/319; 424/324; 544/85; 546/159; 546/174; 546/176; 546/188; 546/190; 546/261; 546/264; 546/265; 546/267; 548/518; 549/59; 549/473; 560/9; 562/426; 564/153

[58] Field of Search ................. 560/9; 562/426; 564/153; 546/188, 190, 159, 174, 176, 261, 264, 265, 267; 544/85; 549/59, 473; 548/518; 424/248.5, 267, 263, 274, 275, 285, 258, 309, 319, 324

[56] References Cited

U.S. PATENT DOCUMENTS

| | | | |
|---|---|---|---|
| 3,574,858 | 4/1971 | Volpp | 564/154 |
| 4,128,721 | 12/1978 | Ondetti | 562/426 |
| 4,153,702 | 5/1979 | Hörlein et al. | 548/518 |
| 4,234,742 | 11/1980 | Cognacq et al. | 562/426 |
| 4,256,761 | 3/1981 | Suh et al. | 562/426 |
| 4,410,542 | 10/1983 | Iwao et al. | 548/518 |

Primary Examiner—Natalie Trousof
Assistant Examiner—Patricia M. Scott

[57] ABSTRACT

Compounds of the structure

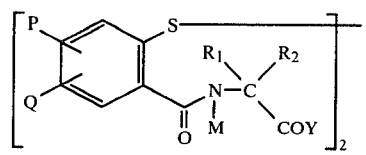

wherein:

P and Q are independently hydrogen, halo, $CF_3$, $OR_1$, $SR_1$, sulfamoyl, alkyl and $NR_1R_2$;

$R_1$ and $R_2$ are independently hydrogen, alkyl, aminoalky, aryl, aralkyl, heteroaryl or cycloalkyl;

Y is OH, $OR_1$, $NH_2$, or, $N(R_1R_2)$; and

M is alkyl, cycloalkyl, aryl, aminoalkyl, aralkyl, heteroaryl or heterocyclic wherein:

the alkyl groups and the alkyl moieties of aminoalkyl, alkoxy and thioalkyl contain from 1 to 6 carbon atoms; the cycloalkyl group contains from 3 to 8 carbon atoms; the aryl group contains from 6 to 10 carbon atoms; the aralkyl group contains from 7 to 16 carbon atoms; and the hetero group is selected from pyrrolidyl, piperidinyl, morpholinyl, pyridyl, quinolinyl, furyl, furfuryl and thienyl; and where Y is a hydroxy, their pharmaceutically acceptable, non-toxic alkali, alkaline earth and amine salts, have angiotensin converting enzyme inhibitory activity.

7 Claims, No Drawings

AROYLAMINOACID DISULFIDES

DESCRIPTION OF THE INVENTION

This invention relates to new chemical compounds possessing valuable pharmaceutical activity. It relates particularly to compounds possessing antihypertensive and angiotensin converting enzyme inhibitory activity and having the structure:

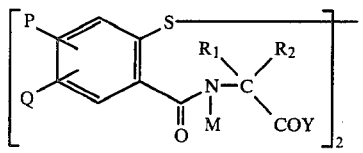

wherein:
P and Q are independently hydrogen, halo, $CF_3$, $OR_1$, $SR_1$, alkyl and $NR_1R_2$;
$R_1$ and $R_2$ are independently hydrogen, alkyl, aminoalkyl, aryl, aralkyl, heteroaryl and cycloalkyl;
Y is OH, $OR_1$, $NH_2$, $N(R_1R_2)$; and
M is alkyl, cycloalkyl, aryl, aminoalkyl, aralkyl, heteroaryl and heterocyclic.

The alkyl group and the alkyl moieties of aminoalkyl, alkoxy, and thioalkyl contain from 1 to 6 carbon atoms. Such groups include methyl, ethyl, propyl, isopropyl, butyl, isobutyl, amyl, isoamyl, hexyl, and the like.

The cycloalkyl groups preferably contain 3 t 8 carbon atoms and include cyclopropyl, cyclobutyl, cyclopentyl, cyclohexyl, cycloheptyl and cyclooctyl.

The aryl groups contain from 6 to 10 carbon atoms and include phenyl, tolyl, xylyl, naphthyl and the like.

The aralkyl groups may contain from 7 to 16 carbon atoms and include benzyl, phenethyl, naphthylmethyl, and the like. The aryl and aralkyl groups may carry substitutents such as halo, $CF_3$, $OR_1$, $SR_1$, alkyl and $NR_1NR_2$.

The hetero groups may be saturated and unsaturated and include pyrrolidyl, piperidinyl, morpholinyl, pyridyl, quinolinyl, furfuryl, thienyl, and the like.

The preferred compounds are those in which:
P and Q are independently hydrogen, halogen, alkyl having 1 to 6 carbon atoms, trifluoromethyl, and alkoxy having 1 to 6 carbon atoms;
$R_1$ and $R_2$ are independently hydrogen, and alkyl having 1 to 6 carbon atoms;
Y is hydroxy, alkoxy having 1 to 6 carbon atoms; where Y is a hydroxy, the suitable salts include the sodium, potassium, ammonium, and calcium salts thereof; and
M is cycloalkyl having 3 to 8 carbon atoms.

The compounds of this invention may be readily prepared in accordance with the following reactions.

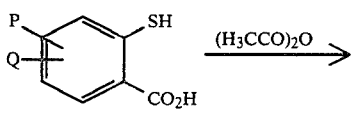

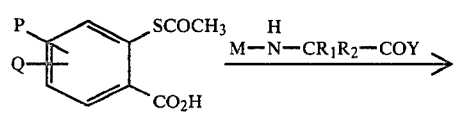

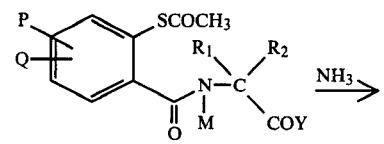

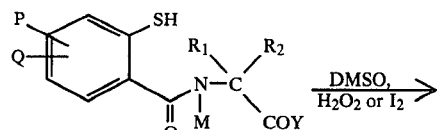

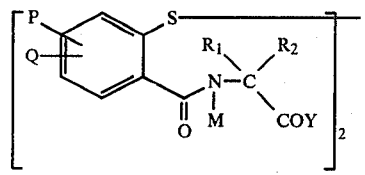

The desired starting materials and intermediates can be prepared from readily available materials using standard organic reactions. Some starting materials and intermediates are also available; for example, from Aldrich Chemical Co., Milwaukee, Wis.

It is known to those skilled in the art that those compounds of the present invention having asymmetric carbon atoms may exist in racemic or optically active forms. All of these forms are contemplated within the scope of the invention.

The invention will be more fully illustrated in the examples that follow. These examples are given by way of illustration and are not to be considered as limiting.

EXAMPLE IA

2-Acetylthiobenzoic acid

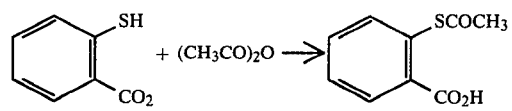

A mixture of 2-mercaptobenzoic acid (5.4 g, 35 mmol) acetic anhydride (4.3 g, 42 mmol) and acetic acid (15 ml) was refluxed 15 minutes. After cooling to room temperature the solution was poured into dilute hydrochloric acid. The product was filtered and recrystallized from toluene, m.p. 127°–129° C.

EXAMPLE IB

N-(2-Acetylthiobenzoyl)-N-cyclopentylglycine

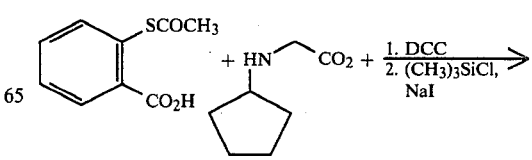

-continued

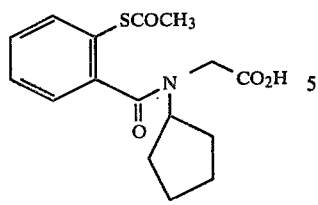

N,N¹-Dicyclohexylcarbodiimide (15.9 g, 77 mmol) in methylene chloride was added slowly to a mixture of 2-acetylthiobenzoic acid (15.2 g, 77 mmol) and N-cyclopentylglycine-t-butyl ester (15.4 g, 77 mmol) in methylene chloride maintained at 0°–5° C. The mixture was brought to room temperature overnight, filtered, and the filtrate washed successively with dilute hydrochloric acid, saturated sodium bicarbonate and saturated sodium chloride solutions. After drying, the organic portion was concentrated, the residue dissolved in ether and the resulting solution filtered. Concentration of the filtrate gave crude N-(2-acetylthiobenzoyl)-N-cyclopentylglycine t-butyl ester as an oil.

The crude ester (28.2 g) was combined with sodium iodide (16.5 g, 0.11 m) in acetonitrile (100 ml) and the mixture brought to 45° C. Chlorotrimethylsilane (11.9 g, 0.11 m) was introduced and heating was continued at 45° C. for 26 min. The mixture was cooled, quenched with water (60 ml) and diluted with methylene chloride. The organic layer was removed, washed with water, sodium thiosulfate solution and brine, and concentrated in vacuo. Treatment of the residue with saturated sodium bicarbonate solution was followed by filtration of insoluble matter. The filtrate was washed with ethyl acetate, acidified (concentrated hydrochloric acid) and extracted (ethyl acetate). Drying and concentration of the extracts gave a residue which was purified by column chromatography or HPLC. The product was isolated as an amorphous solid.

EXAMPLE IC

N-(2-Mercaptobenzoyl)-N-cyclopentylglycine

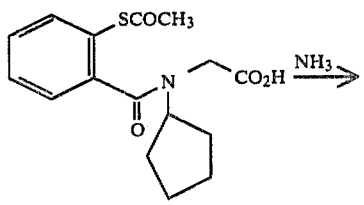

Ammonia gas was bubbled through a solution of N-(2-acetylthiobenzoyl)-N-cyclopentylglycine (5 g, 15 mmol) in methanol (150 ml) for 70 minutes at room temperature. After stirring an additional 20 minutes the solution was concentrated in vacuo and the residue then partitioned between ethyl acetate (200 ml) and 5% sodium bisulfate solution (100 ml). The organic phase was removed, washed with sodium bicarbonate solution and brine, then dried and concentrated. Column chromatographic purification of the residue followed by recrystallization from ethyl acetate afforded white crystalline product, m.p. 148.5°–150° C.

EXAMPLE ID

N-[Bis-2,2'-dithiobenzoyl]-N-cyclopentylglycine

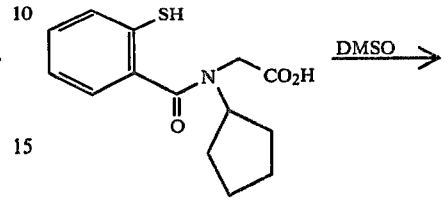

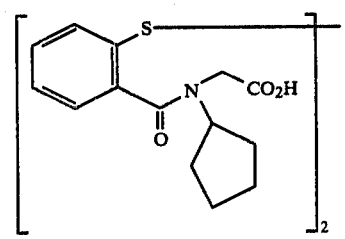

N-(o-Mercaptobenzoyl)-N-cyclopentylglycine (0.5 g, 1.8 mmol) was dissolved in DMSO (0.9 ml) and the solution heated to 80°–100° for 5 hours. After cooling, the mixture was poured into water and the precipitate filtered. HPLC purification provided N-[bis-2,2'-dithiobenzoyl]-N-cyclopentylglycine.

EXAMPLE II

3-Chloro-2-aminobenzoic acid

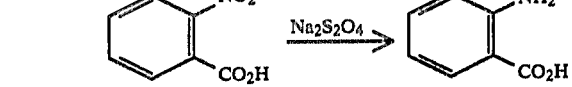

Sodium dithionite (104.4 g, 0.6 m) in water (400 ml) was added in portions to a slurry of 3-chloro-2-nitrobenzoic acid (30 g, 0.15 m) in water (200 ml) containing concentrated ammonium hydroxide solution (10 ml). After stirring an additional 20 minutes the mixture was filtered, acidified to pH 3-4 with concentrated hydrochloric acid and filtered again. The filtrate was saturated with sodium chloride and extracted with ether. Drying and concentration of the extract gave a white powder which was combined with the precipitates above. The crude product was used without further purification.

EXAMPLE IIB

Di(2-Chloro-6-carboxyphenyl)disulfide

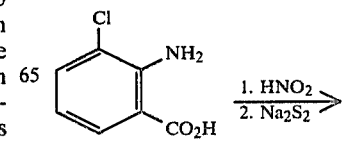

-continued

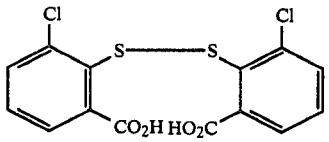

Sodium nitrite (6.9 g, 0.10 m) in water (30 ml) at 0° C. was added in one portion to a slurry of 3-chloro-2-aminobenzoic acid (17.2 g, 0.10 m) in concentrated hydrochloric acid (20 ml)/water (50 ml) containing crushed ice. The mixture was shaken vigorously for several minutes, then filtered. The cold filtrate was slowly added at 0° to a solution of sodium sulfide nonahydrate (26 g, 0.11 m), sulfur (3.4 g, 0.11 m), sodium hydroxide (4.0 g, 0.10 m) and water (40 ml). The mixture was brought to room temperature over several hours, filtered and acidified (concentrated hydrochloric acid) and the disulfide collected by filtration.

EXAMPLE IIC

3-Chloro-2-mercaptobenzoic acid

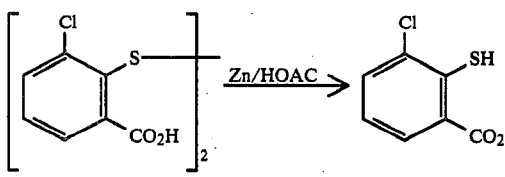

Di(2-chloro-6-carboxyphenyl)disulfide (13.4 g, 35.7 mmole), zinc (7.5 g, 115 mmol) and glacial acetic acid (150 ml) were refluxed one hour; more zinc (7.5 g, 115 mmol) was added, and reflux was continued an additional 3 hours. The mixture was cooled and filtered and the precipitate extracted with hot dilute sodium hydroxide solution. Acidification of the extract (concentrated hydrochloric acid) gave the solid product.

EXAMPLE IID

2-Acetylthio-3-chlorobenzoic acid

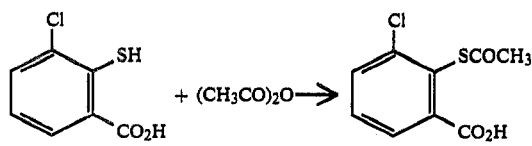

3-Chloro-2-mercaptobenzoic acid (9.8 g, 52 mmol), acetic anhydride (6.3 g, 62 mmol) and glacial acetic acid (22 ml) were heated at 80° C. for 4 hours, then cooled and mixed with dilute hydrochloric acid.
The crystalline product was filtered.

EXAMPLE IIE

N-(2-Acetylthio-3-chlorobenzoyl)-N-cyclopentylglycine t-butyl ester

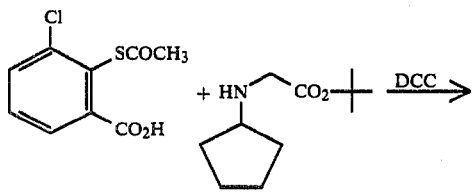

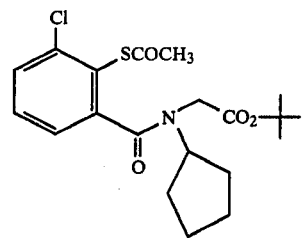

2-Acetylthio-3-chlorobenzoic acid (11.5 g, 50 mmol) and N-cyclopentylglycine t-butyl ester (10.0 g, 50 mmol) in methylene chloride (350 ml) were cooled to 0°-5° C., and N,N¹-dicyclohexylcarbodiimide (10.3 g, 50 mmol) in methylene chloride (50 ml) was added. The mixture was stirred overnight. The DCC-urea was filtered and washed with CH$_2$Cl$_2$. The filtrate was then washed 2×125 ml 1N HCl, 2×125 ml saturated NaHCO$_3$, 2×125 ml brine, dried (MgSO$_4$), filtered and concentrated to give 20.6 g of an oil. The crude product was used without further purification in the next step.

EXAMPLE IIF

N-(2-Thioacetyl-3-chlorobenzoyl)-N-cyclopentylglycine

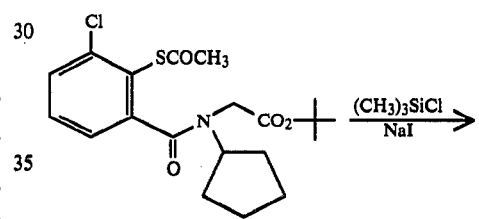

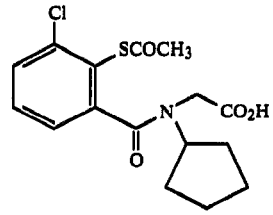

N-(2-Thioacetyl-3-chlorobenzoyl)-N-cyclopentylglycine t-butyl ester (20.6 g, 0.05 mole) was dissolved in 150 ml CH$_3$CN. Sodium iodide (11.3 g, 0.075 m) was then added. The resulting slurry was covered with nitrogen and warmed to 55° C. Chlorotrimethylsilane (8.15 g, 0.075 m) was then added in one portion. The reaction was stirred 30 minutes at 55° C. under nitrogen atmosphere. The heat source was removed and the reaction cooled to room temperature in an ice bath. Water (60 ml) and CH$_2$Cl$_2$ (100 ml) were then added. The aqueous layer was quickly withdrawn and the organic layer washed 2×75 ml H$_2$O, 2×75 ml Na$_2$S$_2$O$_3$ and 2×75 ml brine. The organic layer was then dried (MgSO$_4$), filtered and concentrated to yeild a dark yellow oil.

The oil was dissolved in saturated NaHCO$_3$. The alkaline solution was washed 3×100 ml ethyl acetate. The organic extracts were discarded and the alkaline solution acidified with concentrated HCl. The acidic solution was washed 4×200 ml CH$_2$Cl$_2$, the organic extracts combined, dried (MgSO$_4$) filtered and concentrated to yield 11.2 g (0.032 mole) of an oil which did not crystallize.

Further purification was done using a 12"×1½" silica gel column and eluting with hexane:ethylacetate:acetic acid (5:5:0.3). This afforded 7.4 g of a glassy material. On repeated washing with refluxing hexane this provided an amorphous solid.

C,H,N. theory C: 54.00%; H: 5.10%; N: 3.94%, found C: 51.77%; H: 5.12%; N: 3.79%.

EXAMPLE IIG

N-(2-Mercapto-3-chlorobenzoyl)-N-cyclopentylglycine

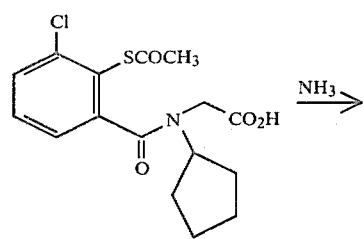
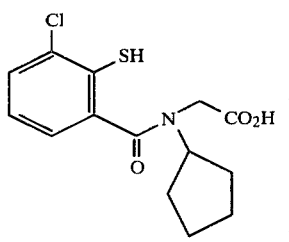

To a chilled solution of methanolic ammonia (50 ml) was added 3.7 g (0.0104 m) of N-(2-thioacetyl-3-chlorobenzoyl)-N-cyclopentylglycine. The reaction was covered with nitrogen and stirred 3 hours while warming slowly from 0° C. to room temperature.

The clear, yellow solution was concentrated in vacuo. The crude material was dissolved in ethyl acetate and washed 2×50 ml 1N HCl, 2×50 ml brine, dried (MgSO$_4$), filtered and concentrated to yield 3.0 g (0.0095 m) of an oil which later solidified. This material was recrystallized from hexane:ethyl acetate (1:1), m.p. 141°-142° C.

C,H,N. theory: C, 53.87%; H, 5.1%; N, 4.46%, found: C, 53.63%, H, 4.94%; N, 4.32%.

EXAMPLE IIH

N-[Bis-2,2'-(dithio-3-chlorobenzoyl)]-N-cyclopentylglycine

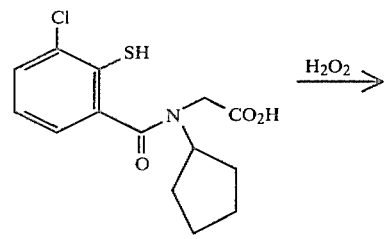

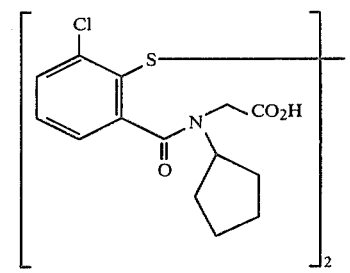

Hydrogen peroxide (50% solution, 1.4 g, 0.02 m) was added to N-(2-mercapto-3-chlorobenzoyl)-N-cyclopentylglycine (4.8 g, 0.015 m) in methanol (50 ml), and the mixture warmed slightly to effect dissolution. After standing several hours, the mixture was concentrated and the precipitate filtered. Recrystallization from methanol afforded N-[bis-2,2'-(dithio-3-chlorobenzoyl)]-N-cyclopentylglycine.

Using procedure described in the preceding examples, the following thiols were converted into disulfides:

EXAMPLE III

N-(2-mercapto-3-methoxybenzoyl)-N-cyclopentylglycine to N,N'-[dithiobis(3-methoxy-2,1-phenylene)-dicarbonyl] bis [N-cyclopentylglycine];

EXAMPLE IV

N-(4-dimethylamino-2-mercaptobenzoyl)-N-cyclopentylglycine to N,N'-[dithiobis(4-dimethylamino-2,1-phenylene) dicarbonyl] bis [N-cyclopentylglycine];

EXAMPLE V

N-(3,5-dichloro-2-mercaptobenzoyl)-N-cyclopentylglycine to N,N'-[dithiobis(3,5-dichloro-2,1-phenylene)dicarbonyl] bis [N-cyclopentylglycine];

EXAMPLE VI

N-(2-mercaptobenzoyl)-N-(p-tolyl)glycine to N,N'-[dithiobis(2,1-phenylene)dicarbonyl] bis [N-(p-tolyl)glycine];

EXAMPLE VII

N-(2-mercaptobenzoyl)-N-cyclopentylalanine to N,N'[dithiobis(2,1-phenylene) dicarbonyl] bis [N-cyclopentylalanine];

EXAMPLE VIII

N-(3-chloro-2-mercaptobenzoyl)-N-furylglycine to N,N'-[dithiobis(3-chloro-2,1-phenylene)dicarbonyl] bis [N-furylglycine];

EXAMPLE IX

N-(2-mercapto-5-trifluoromethylbenzoyl)-N-cyclopentyl-α-phenylglycine to N,N'-[dithiobis(5-trifluoromethyl-2,1-phenylene) dicarbonyl] bis [N-cyclopentyl-α-phenylglycine];

EXAMPLE X

N-(2-mercaptobenzoyl)-N-methylglycine to N,N'-[dithiobis(2,1-phenylene)dicarbonyl] bis [N-methylglycine];

EXAMPLE XI ethyl N-(3-chloro-2-mercaptobenzoyl)-N-cyclopentylglycine to diethyl N,N'-[dithiobis(3-chloro-2,1-phenylene) dicarbonyl] bis [N-cyclopentylglycine].

The compounds of the present invention exhibited angiotensin converting enzyme activity when tested by the methods described in SCIENCE 196, 441-4 (1977), PROC. SOC. EXP. BIOL. MED. 140, 240 (1972) and BIOCHEM. PHARMACOL. 20, 1637 (1971). In vitro activities ranged between 27 to 78% inhibition of angiotensin converting enzyme (ACEI) at 100 μM, while in vivo activities were about 20 to 70% ACE inhibition at a dose of 30 mg/kg. As such, these compounds would be useful in the treatment of hypertension. For example, administration of N,N'-[dithiobis (3-chloro-2,1-phenylene) dicarbonyl]-bis [N-cyclopentylglycine] and diethyl N,N'-[dithiobis (3 chloro-2,1-phenylene) dicarbonyl]-bis [N-cyclopentylglycinate] to sodium deficient hypertensive rats at a dose of 100 mg/kg decreased the blood pressure by 10 to 30% for greater than 24 hours. The compounds of the present invention may be administered orally or parenterally in the treatment of hypertension in the range of about 1 mg/kg to 100 mg/kg of body weight, and it will be within the professional judgment and skill of the practitioner to determine the exact amount to be administered.

What is claimed is:

1. A compound of the structure

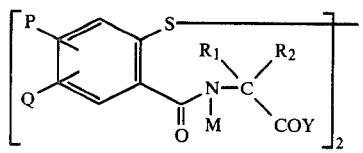

wherein:
P and Q are independently hydrogen, halo, CF$_3$, OR$_1$, SR$_1$, alkyl or NR$_1$R$_2$,
R$_1$ and R$_2$ are independently hydrogen, alkyl, aminoalkyl, aryl, aralkyl, heteroaryl, cycloalkyl, pyrrolidyl, piperidinyl, or morpholinyl;
Y is OH, OR$_1$, NH$_2$, or N(R$_1$R$_2$); and
M is alkyl, cycloalkyl, aryl, aminoalkyl, aralkyl, pyrrolidyl, piperidinyl, morpholinyl, or heteroaryl, wherein:
the alkyl groups and the alkyl moieties of aminoalkyl, alkoxy and thioalkyl contain from 1 to 6 carbon atoms; the cycloalkyl group contains from 3 to 8 carbon atoms; the aryl group contains from 6 to 10 carbon atoms; the aralkyl group contains from 7 to 16 carbon atoms; and the heteroaryl group is selected from pyridyl, quinolinyl, furyl, furfuryl and thienyl; and where Y is a hydroxy, their pharmaceutical acceptable, non-toxic alkali, alkaline earth and amine salts.

2. The compound of claim 1 wherein said aralkyl group in R$_1$, R$_2$ and M is benzyl, phenethyl, or naphthylmethyl.

3. The compound of claim 1 wherein said alkyl groups and the alkyl moieties of aminoalkyl, alkoxy and thioalkyl contain methyl, ethyl, propyl, isopropyl, butyl, isobutyl, amyl, isoamyl or hexyl.

4. The compound of claim 1 wherein said aryl group contains phenyl, tolyl, xylyl or naphthyl.

5. A compound of the structure

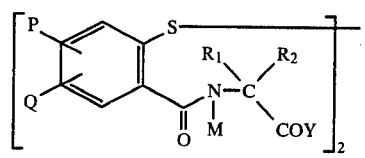

wherein:
P and Q are independently hydrogen, halogen, alkyl having 1 to 6 carbon atoms, trifluoromethyl, or alkoxy having 1 to 6 carbon atoms.
R$_1$ and R$_2$ are independently hydrogen or alkyl having 1 to 6 carbon atoms;
Y is hydroxy or alkoxy having 1 to 6 carbon atoms; and
M is cycloalkyl having 3 to 8 carbon atoms and pharmaceutically acceptable salts thereof.

6. A compound of the structure

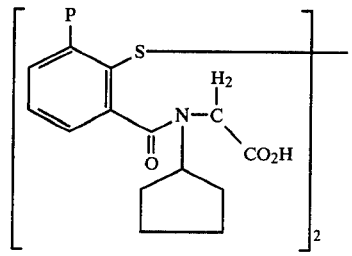

wherein:
P is Cl, F, CH$_3$ or OCH$_3$.

7. A method of treating hypertension in mammals by administering to said mammals an effective amount of a compound of claim 1.

* * * * *